__United States Patent__ [19]

Beck

[11] 4,104,054

[45] Aug. 1, 1978

[54] N[1]-CHLORO-3,5-DINITROSULFANILA-MIDES

[75] Inventor: James Richard Beck, Indianapolis, Ind.

[73] Assignee: Eli Lilly and Company, Indianapolis, Ind.

[21] Appl. No.: 748,856

[22] Filed: Dec. 9, 1976

[51] Int. Cl.[2] .............................................. A01N 9/14
[52] U.S. Cl. ............................... 71/103; 260/397.7 R; 424/228
[58] Field of Search ................. 260/397.7 R, 556 AR, 260/556 B; 71/103; 424/228

[56] References Cited

U.S. PATENT DOCUMENTS

| | | | |
|---|---|---|---|
| 2,328,455 | 8/1943 | Hultquist, et al. | 260/397.7 |
| 3,367,949 | 2/1968 | Soper | 260/397.7 |

*Primary Examiner*—Cecilia M. Jaisle
*Attorney, Agent, or Firm*—Leroy Whitaker; Arthur R. Whale

[57] ABSTRACT

Sodium and potassium salts of N[1]-chloro-3,5-dinitrosulfanilamaides have been prepared. The compounds exhibit potent preemergent herbicidal activity and are also useful for the control of plant fungi, especially *Plasmopara viticola*, the causative organism of downy mildew of grape.

21 Claims, No Drawings

$N^1$-CHLORO-3,5-DINITROSULFANILAMIDES

BACKGROUND OF THE INVENTION

1. Field of the Invention

This invention relates to new chemical compounds. More particularly, this invention relates to sodium and potassium salts of $N^1$-chloro-3,5-dinitrosulfanilamides.

2. Description of the Prior Art

Herbicidal 2,6-dinitroanilines have long been known as evidenced by U.S. patents such as U.S. Pat. Nos. 3,111,403; 3,257,190; and 3,332,769. In U.S. Pat. No. 3,367,949 there is disclosed a class of 2,6-dinitroanilines which are more properly named at 3,5-dinitrosulfanilamides. The compounds of U.S. Pat. No. 3,367,949 serve as starting materials for the preparation of the compounds of the present invention.

Another class of 2,6-dinitroanilines containing a sulfonyl group in the molecule is disclosed in U.S. Pat. No. 3,321,292. However, the compounds there described contain a methylsulfonyl group rather than a sulfonamido group and are only distantly relates to the compounds of the present invention.

SUMMARY OF THE INVENTION

I have now discovered a new group of $N^1$-chloro-3,5-dinitrosulfanilamides having the formula:

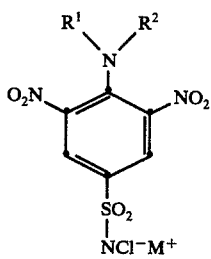

wherein each of $R^1$ and $R^2$ is independently $C_1-C_6$ alkyl, $C_2-C_4$ alkenyl, halo $C_1-C_6$ alkyl or cyclopropyl-methyl; and M is sodium or potassium.

The compounds are useful as preemergent herbicides and in the control of phytopathogenic fungi. A method for the control of undesired vegetation by the application of a herbicidally effective amount of a compound of the present invention and a method for reducing the incidence and severity of grape downy mildew which comprises applying a fungicidally effective amount of a compound of the present invention to the foliage of the host plants are described. Pesticidal compositions comprising a compound as defined above and an inert carrier are also described.

DESCRIPTION OF THE PREFERRED EMBODIMENT

In the above description of my compounds, all of the terms employed have the meanings normally ascribed to them in the chemical art.

The $N^1$-chloro-3,5-dinitrosulfanilamide sodium salts of my invention are prepared by treating the corresponding 3,5-dinitrosulfanilamide with sodium hypochlorite. The preparation of the starting 3,5-dinitrosulfinilamides is described in U.S. Pat. No. 3,367,949.

In preparing the presently claimed compounds a 3,5-dinitrosulfanilamide in a suitable solvent is reacted with sodium hypochlorite in the presence of sodium hydroxide at a temperature between about 0° and 10° C. A suitable solvent is preferably a water miscible solvent in which the 3,5-dinitrosulfanilamide is soluble. A preferred solvent is ethanol. Other suitable solvents include methanol, dioxane, and ethylene glycol dimethyl ether.

A solution of the starting 3,5-dinitrosulfanilamide in the organic solvent is made basic by the addition of aqueous sodium hydroxide solution. The solution is then cooled to a temperature of 0° to 10° C. and aqueous sodium hypochlorite is added. Preferably, a molar excess of between 20 and 100% of sodium hypochlorite is employed although an equimolar amount may be used. After the addition of the sodium hypochlorite is completed the reaction is allowed to proceed for a period of from about 15 minutes to about 2 hours. Generally, the reaction will be complete in about 30 minutes. The product precipitates during the course of the reaction and is collected by a known procedure, such as filtration.

The preparation of exemplary sodium salts of my invention will be illustrated by the following examples. The examples are merely illustrative and do not limit the scope of the compounds of this invention.

EXAMPLE 1

To a solution of 100 g. of 3,5-dinitro-$N^4,N^4$-di-(n-propyl)sulfanilamide in 500 ml. of 3A ethanol and 500 ml. of 2N sodium hydroxide solution cooled to 5° C. was added rapidly dropwise 500 ml. of a 5.25% aqueous solution of sodium hypochlorite. An additional 250 ml. of water was added rapidly dropwise and the mixture was stirred in the cold for one-half hour. The product which had separated was collected by filtration. The yield was 126 g. and the product had a melting point of 88–94° C. It was identified by nuclear magnetic resonance spectroscopy as $N^1$-chloro-3,5-dinitro-$N^4$, $N^4$-di-(n-propyl)sulfanilamide, sodium salt.

Analyses: Calculated for $C_{12}H_{16}N_4O_6SClNa$: C, 35.78; H, 4.00; N, 13.91; Cl, 8.80. Found: C, 35.58; H, 4.25; N, 13.95; Cl, 8.87.

The following additional compounds were prepared following the procedure of Example 1 and using appropriate starting materials. Many of the compounds melt over a board range, probably due to the fact that the compounds are highly solvated.

EXAMPLE 2

$N^1$-chloro-3,5-dinitro-$N^4$-ethyl-$N^4$-methylallyl-sulfanilamide, sodium salt, m.p. 146°–148° C., from 3,5-dinitro-$N^4$-ethyl-$N^4$-methylallylsulfanilamide, yield 74%.

EXAMPLE 3

$N^1$-chloro-3,5-dinitro-$N^4$-ethyl-$N^4$-propylsulfanilamide, sodium salt, m.p. 88°–91° C., from 3,5-dinitro-$N^4$-ethyl-$N^4$-propylsulfanilamide, yield 96%.

EXAMPLE 4

$N^1$-chloro-3,5-dinitro-$N^4$-methylallyl-$N^4$-propyl-sulfanilamide, sodium salt, m.p. 80°–88° C., from 3,5-dinitro-$N^4$-methylallyl-$N^4$-propylsulfanilamide, yield 86%.

EXAMPLE 5

$N^1$-chloro-$N^4$-cyclopropylmethyl-3,5-dinitro-$N^4$-propylsulfanilamide, sodium salt, m.p. 88°–92° C., from $N^4$-cyclopropylmethyl-3,5-dinitro-$N^4$-propylsulfanilamide, yield 100%.

EXAMPLE 6

$N^1$-chloro-$N^4$-chloroethyl-3,5-dinitro-$N^4$-propyl-sulfanilamide, sodium salt, m.p. 83°–88° C., from $N^4$-chloro-ethyl-3,5-dinitro-$N^4$-propylsulfanilamide, yield 86%.

EXAMPLE 7

$N^4$-allyl-$N^1$-chloro-3,5-dinitro-$N^4$-propylsulfanilamide, sodium salt, m.p. 83°–89° C., from $N^4$-allyl-3,5-dinitro-$N^4$-propylsulfanilamide, yield 48%.

EXAMPLE 8

$N^4$-butyl-$N^1$-chloro-3,5-dinitro-$N^4$-ethylsulfanilamide, sodium salt, m.p. 78°–81° C., from $N^4$-butyl-3,5-dinitro-$N^4$-ethylsulfanilamide, yield 34%.

The potassium salts of this invention are prepared by reacting the corresponding sodium salt with potassium hydroxide. The reaction is carried out in a suitable water miscible solvent such as ethanol, methanol, dioxane, or ethylene glycol dimethyl ether. The preferred solvent is ethanol. The reaction is carried out at a temperature ranging from about 0° to about 30° C., preferably 20° to 30° C.

The preparation of potassium salts is illustrated by the following example which is not to be interpreted as limiting the scope of the invention.

EXAMPLE 9

A solution of 5 g. of $N^1$-chloro-3,5-dinitro-$N^4$,$N^4$-di-(n-propyl)sulfanilamide, sodium salt, in 20 ml. of 3A ethanol was added dropwise to 50 ml. of cold 2N potassium hydroxide. The mixture was stirred at room temperature for 40 minutes and then was cooled. The product which separated was collected by filtration. The yield was 3.6 g., m.p. 148°–152° C., dec. It was confirmed by nuclear magnetic resonance spectroscopy and elemental analysis to be $N^1$-chloro-3,5-dinitro-$N^4$,$N^4$-di-(n-propyl)sulfanilamide, potassium salt.

Analyses: Calculated for $C_{12}H_{16}N_4O_6SClK$: C, 34.41; H, 3.85; N, 13.37; Cl, 8.46. Found: C, 34.63; H, 3,98; N, 13.15; Cl, 8.73.

The preferred compounds of my invention are those wherein each of $R^1$ and $R^2$ is $C_1$–$C_6$ alkyl. Particularly preferred are those compounds wherein each of $R^1$ and $R^2$ is independently selected from ethyl, n-propyl and n-butyl. The sodium salts are preferred over the potassium salts.

Another preferred group of compounds are those in which $R^1$ is $C_1$–$C_6$ alkyl, especially ethyl and n-propyl and $R^2$ is $C_2$–$C_4$ alkenyl, especially allyl or methylallyl. Again, the sodium salts are preferred over the potassium salts.

Still another preferred compound is the compound of Example 5.

The compounds of this invention are useful as plant fungicides and herbicides. The compounds are particularly effective in reducing the incidence and severity of grape downy mildew infections when the compounds are applied to the foliage of the host plant in a fungicidally effective amount. The amount of compound which is effective is dependent upon the particular compound employed and the severity of the infection. Preferably, the compounds are applied at a rate of about 10 g. to about 2 kg. per hectare. When a liquid composition is used the active component is preferably present within the range of from about 10 to about 2000 ppm. When dusts are used the active compound is preferably present at from about 0.05 to about 5 percent or more by weight of the composition.

For herbicidal use the compounds are applied preemergently at a rate of from about 0.25 to about 10 kg. per hectare. The compounds may be either incorporated into the soil or surface applied. In general, less compound is required when the soil incorporation method is employed.

For either fungicidal or herbicidal use the present compounds are preferably employed in liquid, powder, or dust compositions containing one or more of such compounds and an inert diluent or carrier. The composition may also contain a surface active agent. Such compositions are prepared in accordance with standard agricultural practices by modifying the present compounds with one or more of a plurality of additaments including organic solvents, petroleum distillates, water or other liquid carriers, surface active dispersing agents, and finely divided inert solids. In such compositions, the active compound can be present in a concentration from about 2 to about 98% by weight.

In the preparation of dust compositions, the chlorosulfanilamides of the present invention can be compounded with any of the finely divided solids such as pyrophyllite, talc, chalk, gypsum, and the like. The finely divided carrier is ground or mixed with the chlorosulfanilamide or wet with a solution of the chlorosulfanilamide in a volatile organic solvent. Dust compositions containing the active compounds of this invention may also be prepared with various solid surface active dispersing agents such as fuller's earth, bentonite, attapulgite, and other clays. Depending upon the proportions of ingredients, these dust compositions can be employed as concentrates and subsequently diluted with an additional solid surface active dispersing agent or with pyrophyllite, chalk, talc, gypsum, or the like to obtain the desired amount of active chlorosulfanilamide. Such dust compositions may also be dispersed in water with or without the aid of dispersing agents to form liquid, sprayable mixtures.

The chlorosulfanilamide compounds or a liquid or dust concentrate composition containing the active compounds can be incorporated in intimate mixture with surface active dispersing agents such as nonionic emulsifying agents to form spray compositions. Such compositions may be employed as such or may be dispersed in liquid carriers to form diluted sprays containing the active compound in any desired amount.

In accordance with standard practice, the active chlorosulfanilamide compound may be compounded with a suitable water immiscible organic liquid and a surface active dispersing agent to produce emulsifiable concentrates which can be further diluted with water and/or oil to form spray mixtures in the form of oil-water emulsions. Preferred dispersing agents to be employed in these compositions are oil soluble and include the nonionic emulsifiers such as condensation products of alkylene oxides with phenols, sorbitan esters, complex ether alcohols, and the like. Suitable organic liquids which can be employed include petroleum oils and distillates, toluene and synthetic organic oils. The surface active dispersing agents are usually employed in liquid compositions in an amount of from about 0.1 to about 20% by weight of the composition.

The herbicidal utility of the compounds of this invention was shown by greenhouse tests using both surface application and soil incorporation methods. The compounds were prepared for use by dissolving in a 1:1 acetone/ethanol solvent containing a small amount of Toximul R and S surfactants. (Toximul R and Toximul S are sulfonate/nonionic blends of emulsifiers for pesticidal formulations. They are manufactured by the Stepan Chemical Company of Northfield, Illinois.) The solutions were diluted with deionized water containing 1000 ppm. Toximul R and S to obtain the desired application rates.

The test plants were grown in galvanized pans 31.5 cm. long, 21.5 cm. wide, and 8.0 cm. deep. Seeds of 14 plants were planted, seven species per pan. The seeds were planted in rows perpendicular to the long axis of the pan, one species per row. The plants employed are as follows:

(A) corn
(B) foxtail millet
(C) grain sorghum
(D) barnyard grass
(E) rice
(F) wild oat
(G) wheat
(H) soybean
(I) pigweed
(J) cotton
(K) jimsonweed
(L) sugar beet
(M) lambsquarters
(N) cucumber For surface application of the test chemicals, the pans were filled two-thirds full with autoclaved greenhouse potting soil. The seeds were laid in rows and were covered with 0.5 to 1.0 cm. of autoclaved soil. The soil surface was then sprayed with the appropriate application rate of the test compound.

For soil incorporation application, the appropriate rate of test compound was mixed into 4.75 l. of autoclaved greenhouse potting soil while the soil was tumbling in a modified cement mixer. Approximately 3.785 l. of treated soil was added to a pan, the seeds were planted in rows perpendicular to the long axis of the pan and were then covered over with the remaining treated soil.

The pans were placed in a greenhouse and the plants were allowed to grow for a period of from 18 to 21 days. The herbicidal effects of the test compounds were then evaluated using a rating scale of 0 to 10, where 0 equals no injury and 10 equals complete kill, with 1 to 9 indicating gradations between the two extremes.

The results obtained with representative compounds of this invention are reported in Tables 1 and 2. The test compounds are identified by their example number while the plant species are identified by the appropriate letter designation. Table 1 reports the soil incorporation results while Table 2 reports the surface application results.

TABLE 1

| Compound No. | Rate kg./ha. | A | B | C | D | E | F | G | H | I | J | K | L | M | N |
|---|---|---|---|---|---|---|---|---|---|---|---|---|---|---|---|
| 1 | 0.56 | 2 | 7 | 3 | 8 | 5 | 3 | 3 | 0 | 7 | 2 | 0 | 3 | 5 | 0 |
|  | 1.12 | 3 | 9 | 4 | 10 | 8 | 5 | 3 | 2 | 10 | 3 | 2 | 7 | 7 | 0 |
|  | 2.24 | 4 | 10 | 9 | 10 | 9 | 6 | 5 | 3 | 10 | 4 | 4 | 7 | 10 | 3 |
| 2 | 0.56 | 2 | 2 | 2 | 8 | 5 | 3 | 2 | 0 | 7 | 0 | 0 | 4 | 3 | 0 |
|  | 1.12 | 4 | 7 | 3 | 9 | 6 | 5 | 3 | 0 | 8 | 0 | 2 | 6 | 9 | 0 |
|  | 2.24 | 3 | 10 | 4 | 10 | 9 | 6 | 4 | 2 | 10 | 3 | 4 | 9 | 10 | 2 |
| 3 | 0.56 | 2 | 6 | 2 | 8 | 5 | 3 | 2 | 2 | 10 | 2 | 2 | 7 | 10 | 0 |
|  | 1.12 | 2 | 10 | 3 | 10 | 8 | 5 | 2 | 2 | 10 | 3 | 3 | 8 | 10 | 2 |
|  | 2.24 | 3 | 10 | 6 | 10 | 9 | 7 | 4 | 3 | 10 | 4 | 5 | 9 | 10 | 3 |
| 4 | 0.56 | 2 | 7 | 3 | 8 | 7 | 3 | 2 | 0 | 7 | 0 | 0 | 8 | 10 | 0 |
|  | 1.12 | 3 | 9 | 4 | 8 | 7 | 2 | 3 | 2 | 10 | 1 | 2 | 7 | 10 | 2 |
|  | 2.24 | 3 | 10 | 7 | 9 | 8 | 4 | 4 | 3 | 10 | 3 | 3 | 9 | 10 | 2 |
| 5 | 0.56 | 0 | 4 | 2 | 7 | 5 | 0 | 2 | 0 | 3 | 0 | 0 | 2 | 3 | 0 |
|  | 1.12 | 2 | 7 | 3 | 8 | 7 | 4 | 3 | 2 | 10 | 2 | 2 | 5 | 10 | 2 |
|  | 2.24 | 4 | 9.5 | 5 | 10 | 8 | 5 | 4 | 2 | 10 | 3 | 3 | 7 | 10 | 3 |
| 6 | 0.56 | 0 | 3 | 2 | 6 | 5 | 2 | 0 | 0 | 7 | 0 | 0 | 2 | 8 | 0 |
|  | 1.12 | 2 | 7 | 3 | 8 | 5 | 3 | 2 | 2 | 10 | 2 | 0 | 3 | 10 | 0 |
|  | 2.24 | 3 | 9.5 | 7 | 8 | 7 | 4 | 4 | 2 | 10 | 2 | 2 | 6 | 10 | 2 |
| 7 | 0.56 | 0 | 2 | 0 | 2 | 3 | 0 | 0 | 0 | 5 | 0 | 0 | 2 | 5 | 0 |
|  | 1.12 | 2 | 5 | 2 | 7 | 5 | 2 | 2 | 0 | 7 | 0 | 0 | 2 | 6 | 0 |
|  | 2.24 | 3 | 9 | 4 | 8 | 7 | 4 | 3 | 0 | 8 | 2 | 2 | 7 | 10 | 0 |
| 8 | 0.56 | 0 | 3 | 2 | 6 | 3 | 0 | 0 | 0 | 6 | 0 | 0 | 2 | 8 | 0 |
|  | 1.12 | 3 | 7 | 3 | 8 | 5 | 2 | 2 | 0 | 9 | 0 | 2 | 5 | 9 | 0 |
|  | 2.24 | 3 | 9.5 | 5 | 9 | 8 | 4 | 3 | 0 | 10 | 3 | 3 | 7 | 10 | 2 |

TABLE 2

| Compound No. | Rate kg./ha. | A | B | C | D | E | F | G | H | I | J | K | L | M | N |
|---|---|---|---|---|---|---|---|---|---|---|---|---|---|---|---|
| 1 | 1.12 | 0 | 9 | 0 | 8 | 3 | 4 | 0 | 2 | 7 | 0 | 0 | 2 | 8 | 0 |
|  | 2.24 | 0 | 9 | 5 | 8 | 4 | 7 | 0 | 3 | 8 | 0 | 0 | 7 | 10 | 0 |
|  | 4.48 | 2 | 10 | 7 | 10 | 8 | 7 | 3 | 4 | 9 | 0 | 2 | 7 | 10 | 0 |
| 2 | 1.12 | 0 | 9 | 0 | 8 | 4 | 4 | 0 | 0 | 7 | 0 | 0 | 4 | 9 | 0 |
|  | 2.24 | 0 | 9 | 4 | 9 | 4 | 7 | 2 | 2 | 7 | 0 | 0 | 5 | 10 | 0 |
|  | 4.48 | 0 | 9.5 | 6 | 10 | 6 | 7 | 3 | 2 | 8 | 2 | 4 | 7 | 10 | 0 |
| 3 | 1.12 | 0 | 9 | 0 | 8 | 3 | 5 | 0 | 0 | 6 | 0 | 0 | 4 | 5 | 0 |
|  | 2.24 | 2 | 9 | 4 | 9 | 8 | 7 | 2 | 0 | 7 | 0 | 2 | 7 | 10 | 0 |
|  | 4.48 | 2 | 9 | 5 | 10 | 8 | 7 | 4 | 0 | 7 | 0 | 3 | 7 | 10 | 2 |
| 4 | 1.12 | 0 | 8 | 0 | 8 | 3 | 4 | 0 | 0 | 6 | 0 | 0 | 3 | 6 | 0 |
|  | 2.24 | 0 | 9 | 2 | 9 | 3 | 5 | 2 | 0 | 7 | 0 | 2 | 3 | 8 | 0 |
|  | 4.48 | 2 | 9 | 4 | 10 | 5 | 7 | 2 | 0 | 8 | 0 | 2 | 6 | 9 | 0 |
| 5 | 1.12 | 0 | 8 | 0 | 8 | 2 | 5 | 0 | 0 | 6 | 0 | 0 | 2 | 6 | 0 |
|  | 2.24 | 0 | 8.5 | 2 | 9 | 3 | 6 | 0 | 0 | 8 | 0 | 0 | 4 | 9 | 0 |
|  | 4.48 | 3 | 9 | 4 | 9 | 5 | 7 | 2 | 3 | 8 | 2 | 3 | 5 | 10 | 0 |
| 6 | 1.12 | 0 | 8 | 2 | 8 | 2 | 2 | 0 | 0 | 6 | 0 | 0 | 0 | 5 | 0 |
|  | 2.24 | 0 | 9 | 3 | 8 | 4 | 4 | 0 | 0 | 8 | 0 | 0 | 4 | 9 | 0 |
|  | 4.48 | 0 | 9 | 5 | 8 | 3 | 6 | 2 | 2 | 7 | 2 | 0 | 5 | 9 | 0 |

TABLE 2-continued

| Compound No. | Rate kg./ha. | SURFACE APPLICATION | | | | | | | | | | | | |
|---|---|---|---|---|---|---|---|---|---|---|---|---|---|---|
| | | A | B | C | D | E | F | G | H | I | J | K | L | M | N |
| 7 | 1.12 | 0 | 8 | 0 | 7 | 0 | 2 | 0 | 0 | 5 | 0 | 0 | 2 | 7 | 0 |
| | 2.24 | 0 | 9 | 2 | 7 | 3 | 2 | 0 | 0 | 7 | 0 | 0 | 2 | 8 | 0 |
| | 4.48 | 0 | 9 | 4 | 9 | 4 | 4 | 2 | 0 | 9 | 0 | 0 | 5 | 10 | 0 |
| 8 | 1.12 | 0 | 8 | 0 | 8 | 3 | 2 | 0 | 0 | 7 | 0 | 0 | 2 | 8 | 0 |
| | 2.24 | 0 | 9 | 3 | 9 | 5 | 3 | 2 | 1 | 7 | 0 | 2 | 5 | 8 | 0 |
| | 4.48 | 2 | 9 | 3 | 9 | 5 | 5 | 2 | 2 | 8 | 0 | 0 | 4 | 8 | 2 |

The usefulness of the compounds of this invention to reduce the incidence and severity of grape downy mildew was also demonstrated in greenhouse tests. The test compounds were formulated by mixing 70 mg. of the compound with 2 ml. of a solution prepared from 500 ml. of acetone, 500 ml. of ethanol, and 100 ml. of Tween 20 (Tween 20 is a polyoxyethylene sorbitan monolaurate made by Atlas Chemical Division of ICI America, Inc., Wilmington, Delaware.) The sample is then diluted with 175 ml. of deionized water containing one drop of Dow Corning antifoam C emulsion per 2 l. of water. (Dow Corning antifoam C is a silicone complex antifoaming agent made by Dow Corning Corporation, Midland, Michigan.) The final formulation contains 400 ppm. of the test compound, 10,000 ppm. of organic solvents, and 1,000 ppm. of Tween 20. This solution may be diluted with deionized water to obtain lower concentrations of the test compound.

On the day the test was started, young expanding leaves were detached from grape vines grown in the greenhouse. One leaf was placed bottom side up in a plastic petri plate containing a Whatman filter paper placed on top of an expanded plastic mat to keep the leaf above the water flooding the bottom of the petri plate. A water soaked wad of cotton was wrapped around the petiole base of the leaf. The test chemical at the desired concentration was sprayed on the underside of the leaf to run off and allowed to dry. As soon as the leaf dried it was innoculated with a conidial suspension of Plasmopara viticola using a DeVilbiss sprayer. Conidia were obtained from recently infected leaf tissue stored in the chill room at 5° C. The conidia were washed off the leaf's surface with a brush and suspended in deionized water to obtain the innoculation suspension.

After innoculation the plates were placed in a moist chamber. Cool white fluorescent lamps above the moist chamber hood provided 200 to 400 foot-candles of light to the leaves on a cycle of 14 hours of light and 10 hours of darkness at 68° F. The leaves were observed for disease symptoms and the results were recorded 7 days after treatment. A rating scale of 1 to 5 was used to record the results where 1 equals severe disease (or no control), 2 equals moderate disease, 3 equals slight disease, 4 equals very slight disease, and 5 equals no disease (or 100% control).

The results of testing representative compounds of this invention are reported in Table 3. Blanks in the table indicate that the compound was not tested at that rate of application.

TABLE 3

| Compound No. | ACTIVITY AGAINST GRAPE DOWNY MILDEW Rate, ppm | | | | | |
|---|---|---|---|---|---|---|
| | 400 | 200 | 100 | 50 | 25 | 12.5 |
| 1 | 5 | 5 | 4+ | 5 | 5 | 4+ |
| 2 | | 4+ | 4+ | 4− | 4 | |
| 3 | | 4+ | 2+ | 2 | | |
| 4 | | 4+ | 3− | 2+ | | |

TABLE 3-continued

| Compound No. | ACTIVITY AGAINST GRAPE DOWNY MILDEW Rate, ppm | | | | | |
|---|---|---|---|---|---|---|
| | 400 | 200 | 100 | 50 | 25 | 12.5 |
| 5 | | 4 | 5 | 3 | | |
| 6 | | 4 | 3− | 3− | | |
| 7 | 4+ | 4+ | 4+ | | | |
| 8 | 5 | 4+ | 5 | 4 | 3− | 1 |

I claim:

1. A compound having the formula

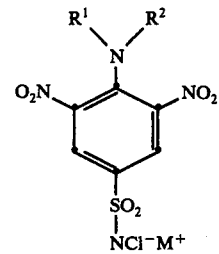

wherein each of $R^1$ and $R^2$ is independently $C_1$–$C_6$ alkyl, $C_2$–$C_4$ alkenyl, halo $C_1$–$C_6$ alkyl or cyclopropylmethyl; and M is sodium or potassium.

2. A compound as in claim 1 wherein each of $R^1$ and $R^2$ is $C_1$–$C_6$ alkyl, and M is sodium.

3. The compound of claim 2 which is $N^1$-chloro-3,5-dinitro-$N^4$,$N^4$-di-(n-propyl)sulfanilamide, sodium salt.

4. The compound of claim 2 which is $N^4$-butyl-$N^1$-chloro-3,5-dinitro-$N^4$-ethylsulfanilamide, sodium salt.

5. A compound as in claim 1 wherein $R^1$ is $C_1$–$C_6$ alkyl, $R^2$ is $C_2$–$C_4$ alkenyl, and M is sodium.

6. The compound of claim 5 which is $N^1$-chloro-3,5-dinitro-$N^4$-ethyl-$N^4$-methylallylsulfanilamide, sodium salt.

7. The compound of claim 5 which is $N^4$-allyl-$N^1$-chloro-3,5-dinitro-$N^4$-propylsulfanilamide, sodium salt.

8. The compound of claim 1 which is $N^1$-chloro-$N^4$-cyclopropylmethyl-3,5-dinitro-$N^4$-propylsulfanilamide, sodium salt.

9. A pesticidal composition comprising a compound of claim 1 and a carrier.

10. A pesticidal composition comprising a compound of claim 2 and a carrier.

11. A pesticidal composition as in claim 10 wherein the compound is $N^1$-chloro-3,5-dinitro-$N^4$,$N^4$-di-(n-propyl)sulfanilamide, sodium salt.

12. A pesticidal composition as in claim 10 wherein the compound is $N^4$-butyl-$N^1$-chloro-3,5-dinitro-$N^4$-ethylsulfanilamide, sodium salt.

13. A pesticidal composition comprising a compound of claim 5 and a carrier.

14. A pesticidal composition as in claim 13 wherein the compound is $N^1$-chloro-3,5-dinitro-$N^4$-ethyl-$N^4$-methylallylsulfanilamide, sodium salt.

15. A pesticidal composition as in claim 13 wherein the compound is $N^4$-allyl-$N^1$-chloro-3,5-dinitro-$N^4$-propylsulfanilamide, sodium salt.

16. A method for the control of undesired vegetation in an area which comprises applying to said area a herbicidally effective amount of a compound of claim 1.

17. A method for the control of undesired vegetation in an area which comprises applying to said area a herbicidally effective amount of a compound of claim 2.

18. A method for the control of undesired vegetation in an area which comprises applying to said area a herbicidally effective amount of a compound of claim 5.

19. A method for reducing the incidence and severity of grape downy mildew which comprises applying to the foliage of the host plant a fungicidally effective amount of a compound of claim 1.

20. A method for reducing the incidence and severity of grape downy mildew which comprises applying to the foliage of the host plant a fungicidally effective amount of a compound of claim 2.

21. A method for reducing the incidence and severity of grape downy mildew which comprises applying to the foliage of the host plant a fungicidally effective amount of a compound of claim 5.

* * * * *